US00PP27391P2

(12) United States Plant Patent
Sakazaki

(10) Patent No.: US PP27,391 P2
(45) Date of Patent: Nov. 15, 2016

(54) ***PETUNIA* PLANT NAMED 'USTUN61801'**

(50) Latin Name: *Petunia×hybrida*
Varietal Denomination: USTUN61801

(71) Applicant: Ushio Sakazaki, Shiga (JP)

(72) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 180 days.

(21) Appl. No.: 14/121,647

(22) Filed: Oct. 1, 2014

(51) Int. Cl.
*A01H 5/02* (2006.01)

(52) U.S. Cl.
USPC ..... Plt./356.2

(58) Field of Classification Search
USPC ..... Plt./356.2
See application file for complete search history.

*Primary Examiner* — Keith Robinson
(74) *Attorney, Agent, or Firm* — C. A. Whealy

(57) ABSTRACT

A new and distinct *Petunia* plant named 'USTUN61801', characterized by its compact, outwardly spreading and mounding to trailing plant habit; freely branching habit; vigorous growth habit; early and freely flowering habit; violet-colored flowers with white-colored throats; and good garden performance.

1 Drawing Sheet

Botanical designation: *Petunia×hybrida.*
Cultivar denomination: 'USTUN61801'.

BACKGROUND OF THE INVENTION

The present invention relates to a new and distinct cultivar of *Petunia* plant, botanically known as *Petunia×hybrida* and hereinafter referred to by the name 'USTUN61801'.

The new *Petunia* plant is a product of a planned breeding program conducted by the Inventor in Higashiomi, Shiga, Japan and Bonsall, Calif. The objective of the breeding program is to create new freely-branching and uniformly mounding *Petunia* plants with early and freely flowering habit, unique attractive flowers and good garden performance.

The new *Petunia* plant originated from a cross-pollination made by the Inventor on May 6, 2011 in Higashiomi, Shiga, Japan of *Petunia×hybrida* 'Brietta Amethyst Blue', not patented, as the female, or seed, parent with *Petunia×hybrida* 'Surfinia Cutie Blue', not patented, as the male, or pollen, parent. The new *Petunia* plant was discovered and selected by the Inventor as a single flowering plant within the progeny of the stated cross-pollination in a controlled greenhouse environment in Bonsall, Calif. on May 24, 2012.

Asexual reproduction of the new *Petunia* plant by vegetative cuttings in a controlled greenhouse environment in Bonsall, Calif. since May 26, 2012 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'USTUN61801'. These characteristics in combination distinguish 'USTUN61801' as a new and distinct *Petunia* plant:

1. Compact, outwardly spreading and mounding to trailing plant habit.
2. Freely branching habit.
3. Vigorous growth habit.
4. Early and freely flowering habit.
5. Violet-colored flowers with white-colored throats.
6. Good garden performance.

Plants of the new *Petunia* can be compared to plants of the female parent, 'Brietta Amethyst Blue'. In side-by-side comparisons conducted in Bonsall, Calif., plants of the new *Petunia* differ primarily from plants of 'Brietta Amethyst Blue' in plant habit as plants of the new *Petunia* are more compact than plants of 'Brietta Amethyst Blue'.

Plants of the new *Petunia* can be compared to plants of the male parent, 'Surfinia Cutie Blue'. In side-by-side comparisons conducted in Bonsall, Calif., plants of the new *Petunia* differ primarily from plants of 'Surfinia Cutie Blue' in the following characteristics:

1. Plants of the new *Petunia* are more mounding than and not as upright as plants of 'Surfinia Cutie Blue'.
2. Plants of the new *Petunia* and 'Surfinia Cutie Blue' differ in flower color as plants of 'Surfinia Cutie Blue' have light blue-colored flowers.

Plants of the new *Petunia* can be compared to plants of 'USTUN29801', disclosed in U.S. Plant Pat. No. 22,883. In side-by-side comparisons conducted in Bonsall, Calif., plants of the new *Petunia* differed primarily from plants of 'USTUN29801' in flower color as plants of 'USTUN29801' have darker violet-colored flowers with violet-colored throats.

Plants of the new *Petunia* can also be compared to plants of 'Kakegawa S28', disclosed in U.S. Plant Pat. No. 13,887. In side-by-side comparisons, plants of the new *Petunia* differed primarily from plants of 'Kakegawa S28' in the following characteristics:

1. Plants of the new *Petunia* had smaller flowers than plants of 'Kakegawa S28'.

2. Plants of the new *Petunia* and 'Kakegawa S28' differed in flower color.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet comprises a side perspective view of a typical plant of 'USTUN61801' grown in a container.

The photograph at the top of the sheet is a close-up view of a typical flowering plant of 'USTUN61801'.

DETAILED BOTANICAL DESCRIPTION

The aforementioned photographs and following observations, measurements and values describe plants grown during the spring in 11.5-cm containers in a polyethylene-covered greenhouse and subsequently in an outdoor nursery in Bonsall, Calif. During the production of the plants, day temperatures averaged 24° C. and night temperatures ranged from 13° C. to 16° C. Plants were pinched two times and were six weeks old when the photographs and description were taken. In the following description, color references are made to The Royal Horticultural Society Colour Chart, 2007 Edition, except where general terms of ordinary dictionary significance are used.

Botanical classification: *Petunia×hybrida* 'USTUN61801'.

Parentage:

*Female, or seed, parent.*—*Petunia×hybrida* 'Brietta Amethyst Blue', not patented.

*Male, or pollen, parent.*—*Petunia×hybrida* 'Surfinia Cutie Blue', not patented.

Propagation:

*Type*.—Terminal vegetative cuttings.

*Time to produce a rooted young plant, summer*.—About 15 days at temperatures ranging from 16° C. to 29° C.

*Time to produce a rooted young plant, winter*.—About 20 days at temperatures ranging from 16° C. to 21° C.

*Root description*.—Medium in thickness, fibrous.

*Rooting habit*.—Freely branching; medium density.

Plant description:

*Plant and growth habit*.—Compact, outwardly spreading and mounding to trailing plant habit; freely branching habit with about 15 primary lateral branches with multiple secondary lateral branches developing per plant; dense and bushy appearance; pinching enhances development of lateral branches; vigorous growth habit.

*Plant height*.—About 13.5 cm.

*Plant diameter* (*area of spread*).—About 32 cm.

*Lateral branches*.—Length: About 18 cm. Diameter: About 3 mm. Internode length: About 1.3 cm. Strength: Strong. Aspect: Initially upright then low spreading. Texture: Densely pubescent. Color: Close to 144B.

Leaf description:

*Arrangement*.—Alternate before flowering; opposite after flowers develop; leaves simple.

*Length*.—About 5.2 cm.

*Width*.—About 2.2 cm.

*Shape*.—Elliptical.

*Apex*.—Broadly acute.

*Base*.—Attenuate.

*Margin*.—Entire.

*Texture, upper and lower surfaces*.—Pubescent.

*Venation pattern*.—Pinnate, arcuate.

*Color*.—Developing leaves, upper surface: Close to 146A. Developing leaves, lower surface: Close to 146B. Fully expanded leaves, upper surface: Close to 137A; venation, close to 146C. Fully expanded leaves, lower surface: Close to 146A; venation, close to 146D.

*Petioles*.—Length: About 1 cm. Diameter: About 3 mm. Texture, upper and lower surfaces: Sparsely pubescent. Color, upper surface: Close to 145A. Color, lower surface: Close to 145B.

Flower description:

*Flower type and flowering habit*.—Single axillary salverform flowers; flowers face mostly upward to outwardly; freely flowering habit with about 15 open flowers per lateral branch and more than 600 flowers developing per plant.

*Natural flowering season*.—Long day responsive; long flowering period, plants flower from early spring until frost in the autumn, flowering continuous during this period; early flowering habit, plants begin flowering about four to six weeks after planting.

*Flower longevity on the plant*.—About four to five days; flowers persistent.

*Fragrance*.—None detected.

*Flower buds*.—Length: About 2.4 cm. Diameter: About 5 mm. Shape: Oblong. Color: Close to N187C.

*Flower diameter*.—About 3.2 cm.

*Flower depth* (*height*).—About 3 cm.

*Throat diameter, distal*.—About 8 mm.

*Tube length*.—About 2.5 cm.

*Tube diameter, proximal*.—About 3 mm.

*Petals*.—Quantity and arrangement: Five petals fused in a single salverform whorl. Petal lobe length (from throat): About 1.8 cm. Petal lobe width: About 1.8 cm. Petal lobe shape: Fan-shaped. Petal lobe apex: Rounded. Petal lobe margin: Entire. Petal lobe texture, upper surface: Smooth, glabrous; velvety. Petal lobe texture, lower surface: Smooth, glabrous. Throat texture: Smooth, glabrous. Tube texture: Pubescent. Color: When opening, upper surface: Close to 83B. When opening, lower surface: Close to 85C. Fully opened, upper surface: Close to brighter and more saturated than 86A; venation, close to N88A; color does not change with development. Fully opened, lower surface: Close to 85C; towards the margins, tints of close to 86C to 86D; venation, close to 194A. Flower throat (inside): Close to NN155B; venation, close to 194D. Flower tube (outside): Close to N155A, venation, close to 194A.

*Sepals*.—Quantity and arrangement: Five sepals fused in a single star-shaped whorl. Length: About 1.7 cm. Width: About 3 mm. Shape: Lanceolate. Apex: Acute. Margin: Entire. Texture, upper and lower surfaces: Pubescent; minute. Color, upper and lower surfaces: Close to 137B.

*Peduncles*.—Length: About 2 cm. Width: About 1 mm. Angle: About 45° to 60° from the stem axis. Strength: Strong. Texture: Pubescent; minute. Color: Close to 145A.

*Reproductive organs*.—Stamens: Quantity per flower: Five. Filament length: About 1.2 cm. Filament color: Close to NN155D. Anther length: About 1 mm. Anther shape: Oval. Anther color: Close to 161C. Pollen amount: None observed. Pistils: Quantity per flower: One. Pistil length: About 1.5 cm. Style length: About 1.1 cm. Style color: Close to 145D. Stigma shape: Round. Stigma color: Close to 145B. Ovary color: Close to 145B.

*Seeds and fruits*.—Seed and fruit development has not been observed on plants of the new *Petunia*.

Pathogen & pest resistance: Plants of the new *Petunia* have not been noted to be resistant to pathogens or pests common to *Petunia* plants.

Garden performance: Plants of the new *Petunia* have been observed to have good garden performance and have been observed to tolerate rain, wind and temperatures ranging from about 1° C. to about 40° C.

It is claimed:

1. A new and distinct *Petunia* plant named 'USTUN61801' as illustrated and described.

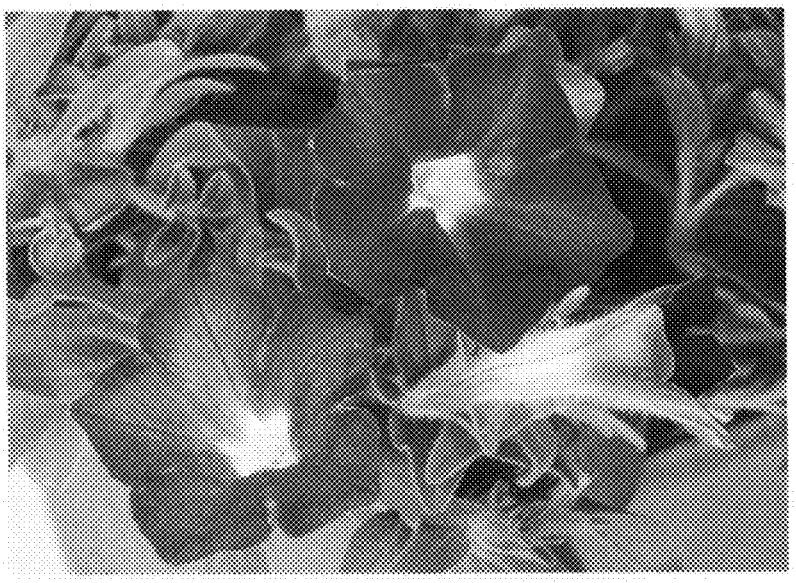
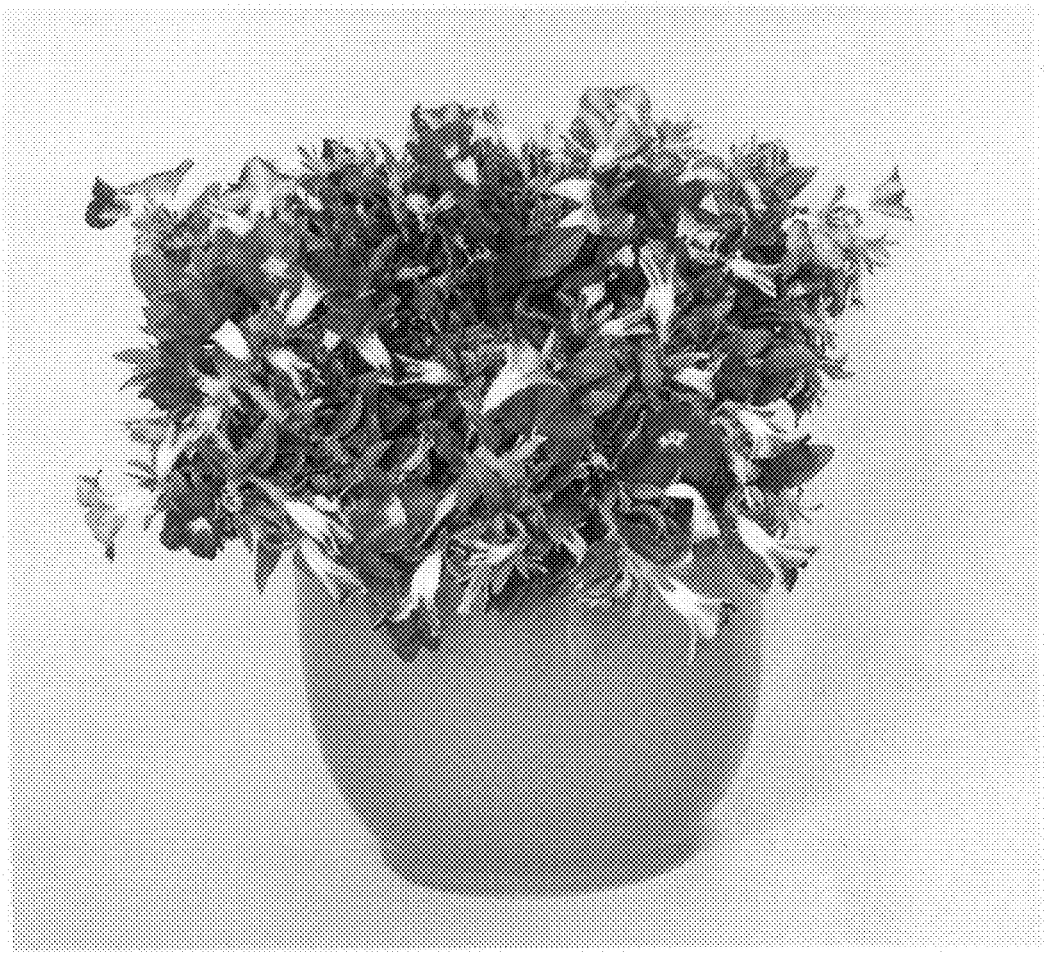

* * * * *